United States Patent [19]
Schotland

[11] Patent Number: 5,747,810
[45] Date of Patent: May 5, 1998

[54] SIMULTANEOUS ABSORPTION AND DIFFUSION TOMOGRAPHY SYSTEM AND METHOD USING DIRECT RECONSTRUCTION OF SCATTERED RADIATION

[75] Inventor: John Carl Schotland, Wynnewood, Pa.

[73] Assignee: Univ. of Pennsylvania

[21] Appl. No.: 449,537

[22] Filed: May 15, 1995

[51] Int. Cl.$^6$ ................................................ G01N 21/64
[52] U.S. Cl. .......................... 250/358.1; 128/633
[58] Field of Search ........................ 250/358.1, 330; 364/413.13; 128/633, 664, 665

[56] References Cited

U.S. PATENT DOCUMENTS

| | | |
|---|---|---|
| 4,515,165 | 5/1985 | Carroll . |
| 4,948,974 | 8/1990 | Nelson et al. . |
| 5,070,455 | 12/1991 | Singer et al. ............ 364/413.19 |
| 5,090,415 | 2/1992 | Yamashita et al. . |
| 5,140,463 | 8/1992 | Yoo . |
| 5,148,022 | 9/1992 | Kawaguchi et al. ............ 250/341 |
| 5,158,090 | 10/1992 | Waldman et al. . |
| 5,203,339 | 4/1993 | Knuttel et al. . |
| 5,213,105 | 5/1993 | Gratton et al. ............ 128/664 |
| 5,270,853 | 12/1993 | Bashkansky et al. . |
| 5,275,168 | 1/1994 | Reintjes et al. . |
| 5,386,827 | 2/1995 | Chance et al. . |
| 5,528,365 | 6/1996 | Gonatas . |

FOREIGN PATENT DOCUMENTS

WO9512132   10/1995   WIPO .

OTHER PUBLICATIONS

"Photon Hitting Density", J.C. Schotland et al., Applied Optics, vol. 32, No. 4, Feb. 1, 1993.

Primary Examiner—David P. Porta
Assistant Examiner—Richard Hanig
Attorney, Agent, or Firm—John T. Peoples

[57] ABSTRACT

A method for the direct reconstruction of an object from measurements of the transmitted intensity of diffusively scattered radiation effected by irradiating the object with a source of continuous wave radiation. The transmitted intensity is related to the absorption and the diffusion coefficients by an integral operator. The images are directly reconstructed by executing a prescribed mathematical algorithm, as determined with reference to the integral operator, on the transmitted intensity of the diffusively scattered radiation.

4 Claims, 8 Drawing Sheets

FIG. 3(iii)
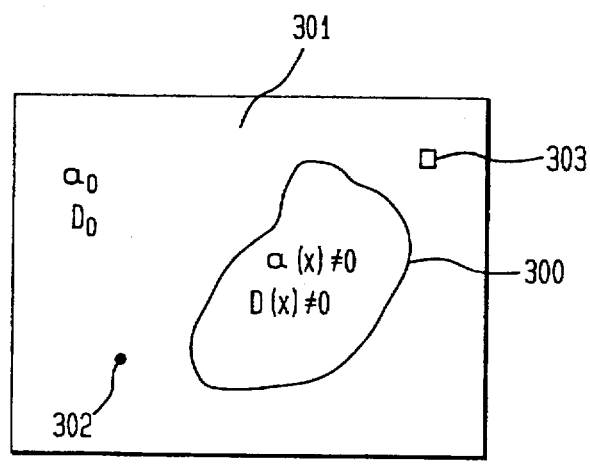

800

```
┌─────────────────────────────────┐
│   FORM KERNEL DENSITY MATRIX S  │
│      OF ORDER 2 x KPQ x N       │
│  (Both ABSORPTION and DIFFUSION)│
└─────────────────────────────────┘
                │  ↘810
                ▼
┌─────────────────────────────────┐
│     COMPUTE SINGULAR VALUE      │
│  DECOMPOSITION OF KERNEL MATRIX │
└─────────────────────────────────┘
                │  ↘820
                ▼
┌─────────────────────────────────┐
│  GENERATE REGULARIZED, GENERALIZED│
│    INVERSE FROM KERNEL MATRIX   │
└─────────────────────────────────┘
                │  ↘830
                ▼
┌─────────────────────────────────┐
│       USE INVERSE TO OBTAIN     │
│    SOLUTION TO COMBINATION OF   │
│      SCHOTLAND's FIRST and      │
│    SECOND INTEGRAL EQUATIONS    │
└─────────────────────────────────┘
                   ↘840
```

FIG. 8

SIMULTANEOUS ABSORPTION AND DIFFUSION TOMOGRAPHY SYSTEM AND METHOD USING DIRECT RECONSTRUCTION OF SCATTERED RADIATION

FIELD OF THE INVENTION

This invention relates generally to a system, and concomitant methodology, for generating images of an object and, more particularly, to such system and methodology for which the images are directly reconstructed from measurements of scattered radiation detected by irradiating the object with a continuous wave source.

BACKGROUND OF THE INVENTION

The inventive subject matter addresses the physical principles and the associated mathematical formulations underlying the direct reconstruction method for optical imaging in the multiple scattering regime. The result is a methodology for the direct solution to the image reconstruction problem. Moreover, the method is generally applicable to imaging with any scalar wave in the diffusive multiple scattering regime and is not limited to optical imaging. However, for the sake of elucidating the significant ramifications of the present invention, it is most instructive to select one area of application of the method so as to insure a measure of definiteness and concreteness to the description. Accordingly, since many biological systems meet the physical requirements for the application of the principles of the present invention, especially diffusion tomography principles, the fundamental aspects of the present inventive subject matter will be conveyed using medical imaging as an illustrative application of the method.

There have been three major developments in medical imaging over the past 20 years that have aided in the diagnosis and treatment of numerous medical conditions, particularly as applied to the human anatomy; these developments are: (1) the Computer-Assisted Tomography (CAT) scan; (2) the Magnetic Resonance Imaging (MRI); and (3) the Positron Emission Tomography (PET) scan.

With a CAT scanner, X-rays are transmitted through, for example, a human brain, and a computer uses X-rays detected external to the human head to create and display a series of images—basically cross-sections of the human brain. What is being imaged is the X-ray absorption function for unscattered, hard X-rays within the brain. CAT scans can detect, for instance, strokes, tumors, and cancers. With an MRI device, a computer processes data from radio signals impinging on the brain to assemble lifelike, three-dimensional images. As with a CAT scan, such malformations as tumors, blood clots, and atrophied regions can be detected. With a PET scanner, the positions of an injected radioactive substance are detected and imaged as the brain uses the substance. What is being imaged is the GAMMA ray source position. Each of these medical imaging techniques has proved invaluable to the detection and diagnosing of many abnormal medical conditions. However, in many respects, none of the techniques is completely satisfactory for the reasons indicated in the following discussion.

In establishing optimal design parameters for a medical imaging technique, the following four specifications are most important. The specifications are briefly presented in overview fashion before a more detailed discussion is provided; moreover, the shortcomings of each of the conventional techniques are also outlined. First, it would be preferable to use a non-ionizing source of radiation. Second, it would be advantageous to achieve spatial resolution on the order of a millimeter to facilitate diagnosis. Third, it would be desirable to obtain metabolic information. And, fourth, it would be beneficial to produce imaging information in essentially real-time (on the order of one millisecond) so that moving picture-like images could be viewed. None of the three conventional imaging techniques is capable of achieving all four specifications at once. For instance, a CAT scanner is capable of high resolution, but it uses ionizing radiation, it is not capable of metabolic imaging, and its spatial resolution is borderline acceptable. Also, while MRI does use non-ionizing radiation and has acceptable resolution, MRI does not provide metabolic information and is not particularly fast. Finally, a PET scanner does provide metabolic information, but PET uses ionizing radiation, is slow, and spatial resolution is also borderline acceptable. Moreover, the PET technique is invasive due to the injected substance.

The four specifications are now considered in more detail. With respect to ionizing radiation, a good deal of controversy as to its effects on the human body presently exists in the medical community. To ensure that the radiation levels are within what are now believed to be acceptable limits, PET scans cannot be performed at close time intervals (oftentimes, it is necessary to wait at least 6 months between scans), and the dosage must be regulated. Moreover, PET is still a research tool because a cyclotron is needed to make the positron-emitting isotopes. Regarding spatial resolution, it is somewhat self-evident that diagnosis will be difficult without the necessary granularity to differentiate different structures as well as undesired conditions such as blood clots or tumors. With regard to metabolic information, it would be desirable, for example, to make a spatial map of oxygen concentration in the human head, or a spatial map of glucose concentration in the brain. The ability to generate such maps can teach medical personnel about disease as well as normal functions. Unfortunately, CAT and MRI report density measurements—electrons in an X-ray scanner or protons in MRI—and there is not a great deal of contrast to ascertain metabolic information, that is, it is virtually impossible to distinguish one chemical (such as glucose) from another. PET scanners have the ability to obtain metabolic information, which suggests the reason for the recent popularity of this technique. Finally, imaging is accomplished only after a substantial processing time, so real-time imaging is virtually impossible with the conventional techniques.

Because of the aforementioned difficulties and limitations, there has been much current interest in the development of a technique for generating images of the distribution of photon absorption and scattering coefficients of living tissue that satisfy the foregoing four desiderata. Accordingly, a technique using low intensity photons would be safe. The technique should be fast in that optical events occur within the range of 10 nanoseconds—with this speed, numerous measurements could be completed and averaged to reduce measurement noise while still achieving the one millisecond speed for real-time imaging. In addition, source and detector equipment for the technique may be arranged to produce necessary measurement data for a reconstruction procedure utilizing appropriately-selected spatial parameters to thereby yield the desired one millimeter spatial resolution. Finally, metabolic imaging with the technique should be realizable if imaging as localized spectroscopy is envisioned in the sense that each point in the image is assigned an absorption spectrum. Such an assignment may be used, for example, to make a map of oxygenation by measuring the absorption spectra for hemoglobin at two different wavelengths, namely, a first wavelength at which hemoglobin is saturated, and a second wavelength at which hemoglobin is de-saturated. The difference of the measurements can yield a hemoglobin saturation map which can, in turn, give rise to tissue oxygenation information.

The first proposals for optical imaging suggested a mathematical approach (e.g., backprojection algorithm) that is similar to that used to generate X-ray computerized tomography images. Light from a pulsed laser is incident on the specimen at a source position and is detected at a detector strategically placed at a point to receive transmitted photons. It is assumed that the earliest arriving photons (the so-called "ballistic photons") travel in a straight line between the source and detector, and the transmitted intensity is used in a mathematical reconstruction algorithm. In effect, only unscattered incident waves are considered as being useful for forming an image of any objects embedded in the specimen and, accordingly, techniques are employed to eliminate scattered light from the detection process, such as arranging a detector with "fast gating time" to only process the earliest arriving photons. However, since it is known that the ballistic photons are attenuated exponentially, if the specimen has a thickness exceeding a predetermined value, imaging is virtually impossible in many practical situations.

The latest proposals for optical imaging are now directed toward imaging systems which use scattered and diffused radiation to reconstruct a representation of the interior of a specimen. Representative of prior art in this field is U.S. Pat. No. 5,070,455 issued to Singer et al (Singer) on Dec. 3, 1991. The system disclosed by Singer uses radiation, such as photons or other particles, which will be scattered to a significant degree by the internal structure of a specimen. In the system, a specimen is irradiated and measurements of the attenuated and scattered radiation are effected at a number of points along the exterior of the specimen. It has been determined by Singer that such measurements are sufficient to determine the scattering and attenuation properties of the various regions inside the specimen. In accordance with the disclosure of Singer, the interior of the specimen is modeled as an array of volume elements ("voxels"). Each voxel in the model of the specimen has scattering and attenuation properties which are represented by numerical parameters that can be mapped so as to generate several images of the interior of the specimen.

The particular technique used by Singer to reconstruct the interior of the specimen can best be characterized as an "iterative" procedure. This procedure is now described in some detail so as to pinpoint its shortcomings and deficiencies. After collecting the imaging data, the scattering and attenuation coefficients for the voxels are assigned initial values, which helps to shorten the computation process—but which is also the characteristic of iterative or non-direct solution to a mathematical minimization problem. Next, the system computes the intensity of light that would emerge from the specimen if the interior of the object were characterized by the currently assigned values for the scattering and attenuation coefficients. Then, the difference between the measured light intensities and the computed light intensities are used to compute an "error function" related to the magnitude of the errors of reconstruction. This error function (also called "cost function" in minimization procedures) is then minimized using a multi-dimensional gradient descent methodology (such as Fletcher-Powell minimization), i.e., the coefficients are modified so as to reduce the value of the error function.

The process of computing exiting light intensities based on the currently assigned values for the scattering and attenuation coefficients, and then comparing the differences between the computed values and measured values to generate a new approximation of the scattering and attenuation properties of the interior of the specimen, continues until the error function falls below a specified threshold. The final values of the scattering and attenuation coefficients from this process are then mapped so as to generate a series of images of the interior of the specimen, thereby depicting the attenuation and scattering characteristics of the specimen's interior—which presumably will disclose both normal and abnormal conditions.

Singer thus discloses a technique to reconstruct an image by inversion using an iterative minimization procedure. Such an approach is more formally characterized as a "heuristic", in contrast to an "algorithm", since no verification or proof of even the existence of a solution using the approach has been offered. There are essentially an infinite number of scattering and attenuation coefficients under such a regime, and there is absolutely no assurance that the particular coefficients determined using the iterative technique are the actual coefficients for the specimen's interior. Moreover, such a heuristic method has a high computational complexity which is exponential in relation to the number of voxels and which is, in turn, a characteristic of difficult optimization problems with many local minima. The computational complexity of such a approach renders the reconstruction method virtually useless for imaging.

There are other approaches presented in the prior art which are closely related to that presented by Singer; these approaches also effect an indirect inversion of the forward scattering problem by an iterative technique which provide little, if any, physical insight.

Representative of another avenue of approach in the prior art is the subject matter of U.S. Pat. No. 5,213,105 issued to Gratton et al (Gratton). With this approach, a continuous wave source of amplitude modulated radiation irradiates an object under study, and radiation transmitted or reflected by the object is detected at a plurality of detection locations, as by a television camera. The phase and the amplitude demodulation of the radiation is detected, and a relative phase image and a demodulation amplitude image of the object are generated from, respectively, the detected relative phase values and detected demodulation amplitudes of the radiation at the plurality of locations. However, while Gratton does generate data from a continuous wave source, there is no teaching or suggestion of a methodology to use the data to directly reconstruct the image from the data—rather the data of Gratton is merely used to obtain and display, separately and independently, the shift in relative phase and the change in modulation of the wavefront of amplitude modulated radiation as a result of propagation of radiation through a scattering medium. Thus, there is no teaching or suggestion in Gratton of how the totality of the spatial modulation and phase data can be combined in a unified approach to directly reconstruct the image. It should be noted that at high modulation frequencies the Gratton procedure is essentially equivalent to ballistic imaging, while at low modulation frequencies an entirely new approach to the reconstruction problem is necessary.

SUMMARY OF THE INVENTION

These limitations and other shortcomings and deficiencies of conventional techniques are obviated, in accordance with the present invention, by utilizing a direct reconstruction methodology, and concomitant system, to generate an image of an object under investigation; the direct reconstruction formulation guarantees both the existence and uniqueness of the imaging technique. Moreover, the direct reconstruction method significantly reduces computational complexity.

In accordance with the broad aspect of the present invention, the object under study is irradiated by a continuous wave source at a given frequency and the transmitted intensity due predominantly to diffusively scattered radiation is measured at selected locations proximate to the object wherein the transmitted intensity is related to both the absorption and diffusion coefficients by an integral operator. The absorption and diffusion images of the object are directly reconstructed by executing a prescribed mathematical algorithm, determined with reference to the integral operator, on the transmitted intensity measurements. In addition, radiation at different wavelengths effects imaging as localized spectroscopy.

The organization and operation of this invention will be understood from a consideration of the detailed description of the illustrative embodiment, which follows, when taken in conjunction with the accompanying drawing.

BRIEF DESCRIPTION OF THE DRAWING

FIG. 8 is a flow diagram depicting one methodology for computing the absorption and diffusion coefficients of the object under investigation.

The same element appearing in more than one FIG. has the same reference numeral.

DETAILED DESCRIPTION

To place in perspective the detailed description of the present invention and thereby highlight the departure from the art as disclosed and claimed herein, it is both instructive and informative to first gain a basic understanding of the imaging environment in which the present invention operates by presenting certain foundational principles pertaining to the subject matter in accordance with the present invention. Accordingly, the first part of the description focuses on a high-level discussion of the imaging systems relevant to the inventive subject matter; this approach has the advantage of introducing notation and terminology which will aid in elucidating the various detailed aspects of the present invention. After this overview, the system aspects of the present invention, as well as the concomitant methodology, are presented with specificity.

OVERVIEW OF THE PRESENT INVENTION

Multiple scattering of light presents a fundamental physical obstruction to optical imaging. The inventive subject matter of the present invention addresses this phenomena, with the surprising result that diffusive light contains sufficient information to image the optical absorption and optical diffusion coefficients of a highly scattering medium. This conclusion obtains from a version of inverse scattering theory that is applicable to multiple scattering in the diffusion limit. Using this representation, the first direct reconstruction procedure ever devised for imaging the optical absorption and optical diffusion coefficients of a highly scattering medium probed by diffusing waves is elucidated. In contrast to techniques which utilize unscattered (ballistic) photons for image formation, the procedure in accordance with the present invention allows for the imaging of objects whose size is large compared to the average scattering mean free path.

The familiar opaque or cloudy appearance of many objects having impinging light may be explained by the phenomenon of multiple light scattering. (It is to be noted that terminology will be generalized hereinafter so that an "object" is the physical manifestation of what is under study—such an object may stand alone, may be embedded in a specimen or a sample; in any case, the context of the descriptive material about an object will be set forth with clarity the meaning to be attached to the generic term "object" in that context.) The disclosure and teachings of the present invention address the problem of imaging an extended object that is embedded in a highly scattering medium. Since diffusively transmitted light contains sufficient information for direct image reconstruction, the problem can be expressed in a tractable form amenable to an essentially closed-form solution—meaning that there is no need to rely upon or resort to an iterative/minimization-type reconstruction with all its shortcomings and pitfalls.

Figure 1:
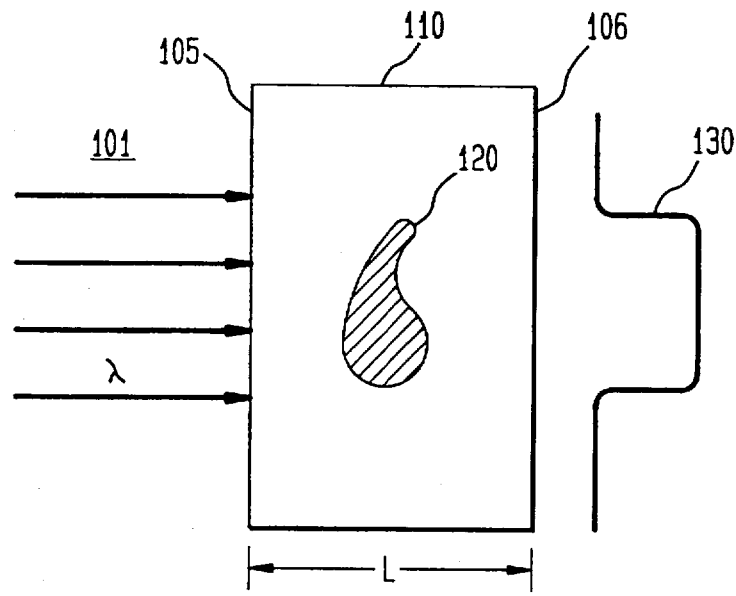
FIG. 1 exemplifies the transmission of light through a specimen containing an absorbing object in the ballistic limit.

For illustrative purposes, the case of only an absorbing object is considered. To elucidate the direct reconstruction process at its most fundamental level, a simplified absorbing system to which direct reconstruction is applicable is first described, namely, one in which a plane wave of light (photons) of wavelength $\lambda$ is incident upon a sample of linear dimension L that contains a spatially-extended object characterized by a position-dependent optical absorption coefficient; the width L is aligned with the impinging incident wave. If it is further assumed that photons are scattered by particles whose size is large compared to $\lambda$, then the scattering is described by a transport mean free path, designated l*; the mean free path characterizes the average distance a photon travels before its direction is randomized. In the single-scattering regime, that is, where l*>>L, it is observed that most of the incident wave is unscattered upon exiting the sample and thus may be used to form a projection image of the absorbing object; this effect is depicted in FIG. 1. In FIG. 1, light rays 101 of wavelength $\lambda$ impinge on front 105 of sample 110 containing absorbing object 120, wherein the light rays transmitted through sample 100 exiting back 106 of sample 110 form a projection image represented by trace 130. The transmitted intensity represented by trace 130 is related to line integrals of the optical absorption coefficient along the direction of propagation of the unscattered wave. This gives rise to the so-called Radon transform of the absorption coefficient. By inversion of the Radon transform, it is possible to recover the absorption function and thus an image of absorber 120 is reconstructed. As already alluded to above, all commercially available imaging techniques are based on this simple physical principle.

Figure 2:
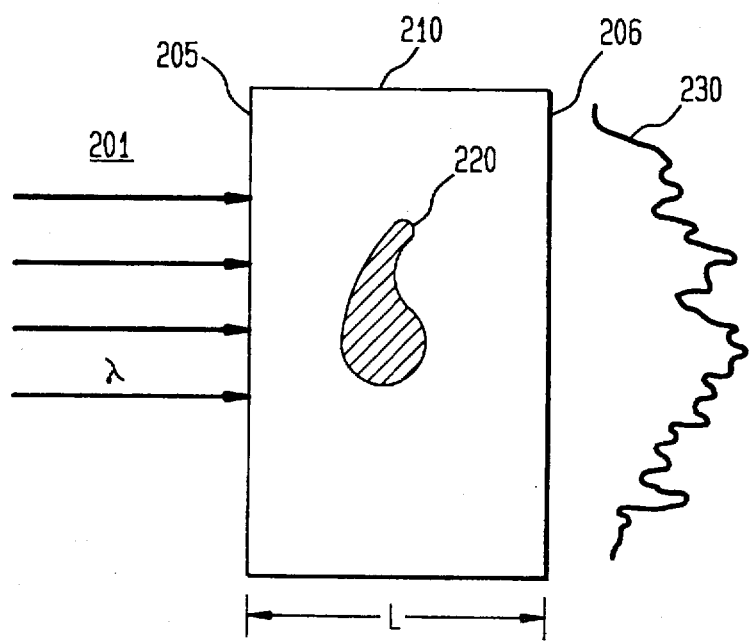
FIG. 2 exemplifies the transmission of light through a specimen containing an absorbing object in the diffusion limit.

In the multiple-scattering regime, that is, where $l^* \ll L$, a wave scatters many times while traversing the sample. In this situation, with $\lambda \ll l^*$, the path of a single photon may be described as a diffusive random walk where $D=\frac{1}{3}(c/n)l^*$ is a suitable diffusion constant, with c being the speed of light, n being the index of refraction, and c/n being the speed of light in the medium of the sample. The unscattered, or ballistic photons, are exponentially attenuated with a static transmission coefficient $T_{ball} \sim \exp(-L/l^*)$. The dominant contribution to the transmitted intensity is provided by diffusive photons with a diffusive transmission coefficient $T_{diff} \sim l^*/L$ which, even with coherent illumination, forms a complicated interference pattern that does not contain a simple image of the sample; such a pattern is illustrated in FIG. 2 (which has essentially the same pictorial representation as FIG. 1, except that the physical system of FIG. 2 is such that $l^* \ll L$ as contrasted to $l^* \gg L$ in FIG. 1). In FIG. 2, light rays 201 of wavelength $\lambda$ impinge on front 205 of sample 210 and eventually exit sample 210 from back 206. Absorbing object 220 gives rise to trace 230, which is representative of the complicated transmitted light pattern exiting back 206. In accordance with the present invention, there is devised a closed-form procedure for utilizing the information in such complicated patterns as exhibited by trace 230 to locate an object and thus perform optical imaging in the multiple-scattering regime.

Indeed, it has frequently been pointed out in the prior art that ballistic photons convey the least distorted image information while diffusive photons lose most of the image information. For this reason several elegant experimental techniques have been designed to select the ballistic photon contribution either by optical gating, holography, or filtering of the diffusive photons by optical absorption. There is, however, an intrinsic physical limitation of any technique that relies solely on ballistic photons. This may be appreciated by considering the exponential attenuation of ballistic photons relative to the mild algebraic attenuation of diffusive photons. In particular, if the sample size L is sufficiently large compared to $l^*$, then $T_{ball}$ will fall below an experimentally measurable threshold (e.g., if $l^*$ is about 0.5 millimeters, then the attenuation is proportional to $e^{-40}$ in only 2 centimeters).

Thus, the likelihood of now reconstructing important and valuable images heretofore believed to be virtually impossible to reconstruct provides a strong motivation to overcome the limitations of ballistic imaging by employing multiply scattered diffusive photons for image reconstruction. From fundamental physical principles, such a reconstruction from the interference pattern of diffusive transmitted light is attainable since such reconstruction is uniquely determined by two parameters, namely, the absorption and diffusion coefficients of the highly scattering system. As presented herein in accordance with the present invention, the diffusive transmission coefficient is related to both the absorption and diffusion coefficients by an integral equation. Then the absorption and diffusion images may be directly reconstructed using a suitable algorithm which references this integral operator. In contrast to ballistic methods, the resulting reconstruction may be used to image samples whose size L is large compared to $l^*$.

FUNCTION THEORETIC BASIS FOR ABSORPTION AND DIFFUSION IMAGING

Consider the propagation of a diffusing wave in a highly scattering medium, characterized by both fluctuations in the absorption and diffusion coefficients, due to an amplitude-modulated (AM), continuous wave (CW) source. As an example, such a source may be expressed as $S(x,t)=(1+Ae^{i\omega t})S(x)$, where $S(x,t)$ is the source power density, $\omega$ is the radian frequency of the continuous wave, and generally $A<1$. Typically, for $\omega=2\pi f$, f is in the radio frequency (RF) range of 100 MHz to 1 GHz. For a point source at the origin, $S(x)=S_0\delta(x)$ where $S_0$ is the source power. Only the behavior of the energy density of the system is considered.

Figure 3I:
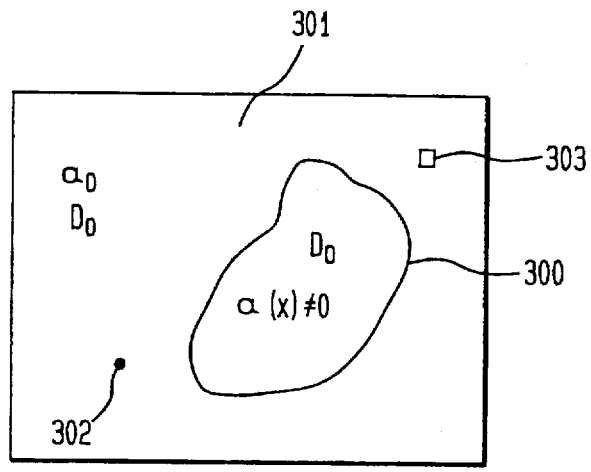
FIG. 3 depicts an object embedded in a medium for the cases of constant diffusion, constant absorption, and fluctuating diffusion and absorption, respectively.
Figure 3:
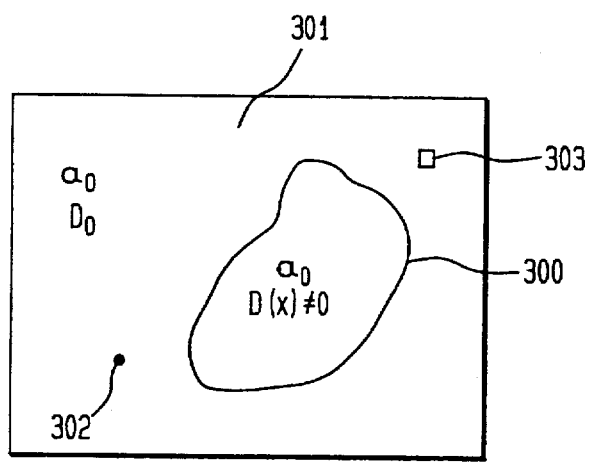

The energy density $u(x,t)$ of a diffusing wave for fluctuations in both the absorption and the diffusion coefficients obeys the following relation:

$$\partial_t u(x,t) = \nabla((D_0+D(x))\nabla u(x,t) - (\alpha_0+\alpha(x))u(x,t)+S(x,t), \quad (1)$$

where $\alpha_0$ is the background absorption of the medium, $\alpha(x)$ is the fluctuation in absorption away from the background, $D_0$ is the background diffusion of the medium, and $D(x)$ is the fluctuation in diffusion away from the background. The diagram of FIG. 3 (iii) depicts these relations, namely, object 300 is shown immersed in medium 301 which has absorption $\alpha_0$ and diffusion constant $D_0$; object 300, on the other hand, has absorption $\alpha(x) \neq 0$ and diffusion $D(x) \neq 0$. (Also shown for completeness is $i^{th}$ source 302 and $j^{th}$ detector 303 surrounding object 300, as discussed in detail shortly).

Since only the long-time solution to the diffusion equation expressed in equation (1) is of concern, a solution of equation (1) in the following form is expected:

$$u(x,t)=u_0(x)+Ae^{i\omega t}u_\omega(x), \quad (2)$$

where $u_0(x)$ is the zero frequency (DC) solution and $u_\omega(x)$ is the oscillatory (AC) solution at the angular frequency $\omega$.

In a typical experiment, $u_{ac}(x,t)$ is derived from measurements where:

$$u_{ac}(x,t)=e^{i\omega t}u_\omega(x). \quad (3)$$

It is noted that $u_{ac}(x,t)=|u_\omega(x)|e^{i(\omega t+\phi(x))}$ and that $|u_\omega(x)|$ (the "modulus") and $\phi(x)$ (the "phase") are separately measurable with appropriate detectors, as discussed shortly.

The relation expressed in equation (3) leads to the following definition of transmission coefficient—defined as the transmitted intensity through the absorbing and diffusing medium when the incident wave has unit flux:

$$T_{ac}=u_{ac}(x)_{ac}{}^0(x)=u_\omega(x)/u_\omega{}^0(x), \quad (4)$$

where $u_\omega{}^0(x)$ is the oscillatory part of the energy density when the absorbing object is not present. Thus, based on equation (4), it is sufficient to determine $u_\omega(x)$ to obtain $T_{ac}$. Accordingly, it can be shown in the weak fluctuation limit that:

$$-\ln T_{ac}(x_1,x_2) = \int d^3x \Gamma_A(x;x_1,x_2)\alpha(x)+\int d^3x \Gamma_D(x;x_1,x_2)D(x), \quad (5)$$

where, in the weak fluctuation limit, $\Gamma_A$ and $\Gamma_D$, the "absorption kernel" and the "diffusion kernel", respectively, are given by:

(1) Absorption Kernel $$\Gamma_A(x; x_1,x_2) = \frac{1}{G_0(x_1,x_2)} G_0(x_1,x)G_0(x,x_2). \quad (6)$$

Here, $G_0(x,x')$ is the unperturbed Green's function for the diffusing wave, which in an infinite medium has the following form:

$$G_0(x,x') = \frac{\exp[-k(\omega)|x-x'|]}{4\pi D_0|x-x'|} \quad (7)$$

where $$k(\omega) = \left( \frac{\alpha_0 + i\omega}{D_0} \right)^{\frac{1}{2}} \qquad (8)$$

(2) Diffusion Kernel $$\Gamma_A(x; x_1, x_2) = \frac{1}{G_{a0}(x_1, x_2)} \nabla_x G_0(x_1, x) \nabla_x G_0(x, x_2). \qquad (9)$$

An analytical expression for $\Gamma_A(x;x_1,x_2)$ for an infinite medium may be obtained with the result $$\Gamma_A(x; x_1, x_2) = \qquad (10)$$

$$\frac{1}{4\pi D_0} \frac{|x_1 - x_2|}{|x - x_1||x - x_2|} \exp[-k(\omega)(|x - x_1| + |x - x_2|)].$$

Figure 4A:
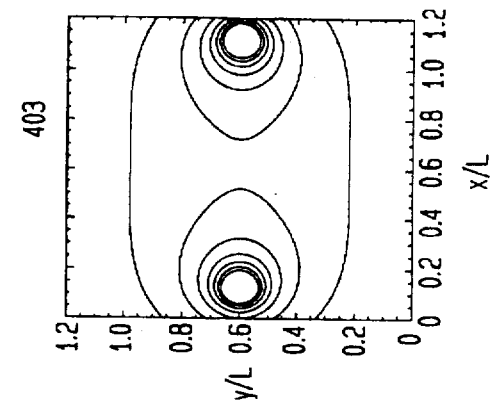
FIG. 4 depicts plots of the absorption kernel and the diffusion kernel.
Figure 4B:
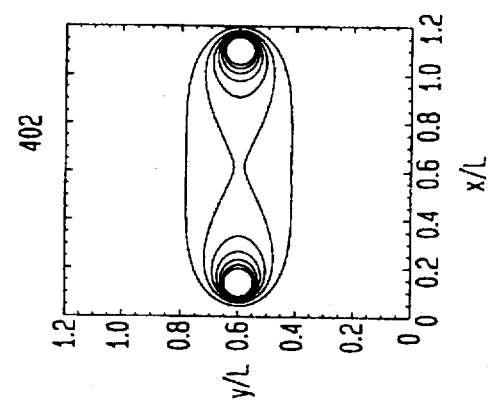
Figure 4C:
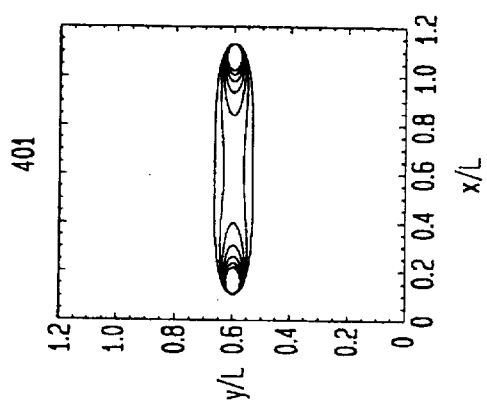

Contour plots of $\Gamma_A(x;x_1,x_2)$ are shown in FIG. 4 for various exemplary values of $\omega\tau_D$, where $\tau_D=L^2/D$; in particular, FIGS. 4(a)–4(c) show $\Gamma_A(x;x_1,x_2)$ for $\omega\tau_D$ equal to $10^4$, $10^2$, and 1, respectively. As depicted, at high frequencies (FIG. 4(i)) the kernel 401 is largely concentrated on the line connecting the source and detector. At lower frequencies (FIGS. 4(b) and 4(c)), in the multiple scattering regime, the kernel (402 and 403, respectively) accounts for more extensive spatial contributions.

An analytical expression for $\Gamma_D(x;x_1,x_2)$ for an infinite medium may be obtained with the result $$\Gamma_D(x; x_1, x_2) = \frac{1}{4\pi D_0} \frac{(x-x_1)(x-x_2)|x_1-x_2|}{(x-x_1)^2(x-x_2)^2} \left[ \frac{1}{|x-x_1|} + k(\omega) \right] \left[ \frac{1}{|x-x_2|} + k(\omega) \right] \times \qquad (11)$$

$$\exp[-k(\omega)(|x - x_1| + |x - x_2| - |x_1 - x_2|)].$$

Figure 4D:
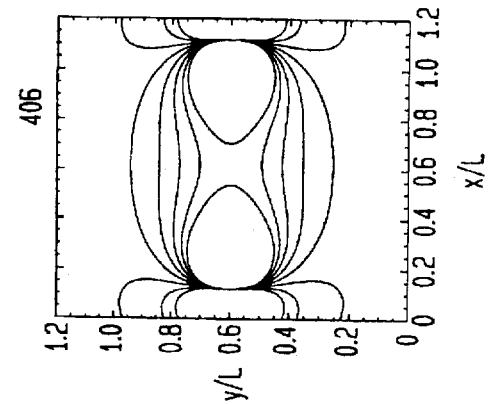
Figure 4E:
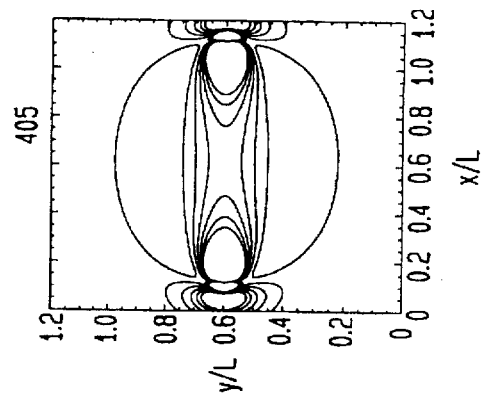
Figure 4F:
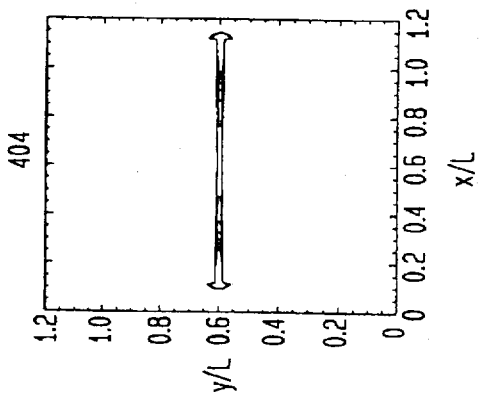

Contour plots of $\Gamma_D(x;x_1,x_2)$ are shown in FIG. 4 for various exemplary values of $\omega\tau_D$, where $\tau_D=L^2/D$; in particular, FIGS. 4(d)–4(f) show $\Gamma_D(x;x_1,x_2)$ for $\omega\tau_D$ equal to $10^4$, $10^2$, and 1, respectively. As depicted, at high frequencies (FIG. 4(d)) the diffusion kernel 404 is largely concentrated on the line connecting the source and detector. At lower frequencies (FIGS. 4(e) and 4(f)), in the multiple scattering regime, the kernel function (405 and 406, respectively) accounts for more extensive spatial contributions.

Integral equation (5) relates the transmission coefficient of the diffusing wave to the absorption and the diffusion coefficients. Equation (5) is valid in the limit of small spatial fluctuations in absorption and diffusion.

Figure 5I:
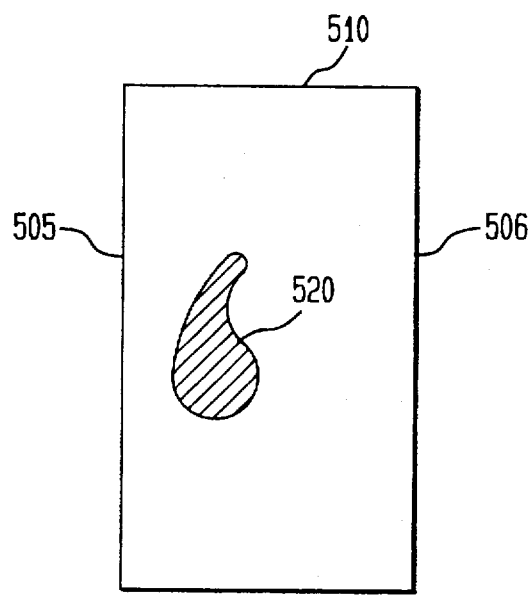
FIG. 5 illustrates an object in a medium and a simulated reconstruction of the object using the direct reconstruction technique of the present invention.
Figure 5:
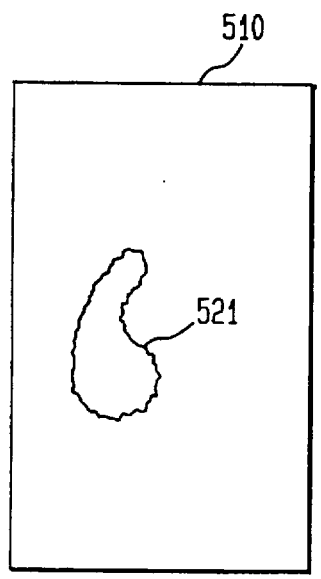

The direct reconstruction of a two-dimensional object using computer processing on simulated transmission data is shown in FIG. 5; the reconstructed object of FIG. 5 serves as a pictorial visualization of the effectiveness of the direct reconstruction process. In FIG. 5(i), object 520 is shown as embedded in medium 510. Since the shape of object 520 is known, it is possible to mathematically describe, and thereby to calculate the emanation of photons from back 506 due to photons impinging on front 505, that is, solve the so-called forward problem in diffusing wave imaging. Given the transmission intensity of photons detected proximate to back 506, the so-called inverse problem can be solved to directly reconstruct an image of object 520—such a directly reconstructed image is depicted by object 521 in FIG. 5(ii). It is important to emphasize that, although the transmission data is simulated, the algorithm used in the computer processing to reconstruct image 521 is the very one used to process actual measurements of transmission intensity detected from an actual sample. Such simulations afford the opportunity to study, for example, noise effects on the transmission intensity data and sensitivity of the reconstruction technique to the various locations of the source-detector pair.

DETAILS OF THE ABSORPTION AND DIFFUSION IMAGING ASPECT OF THE PRESENT INVENTION

A. SYSTEM

Figure 6:
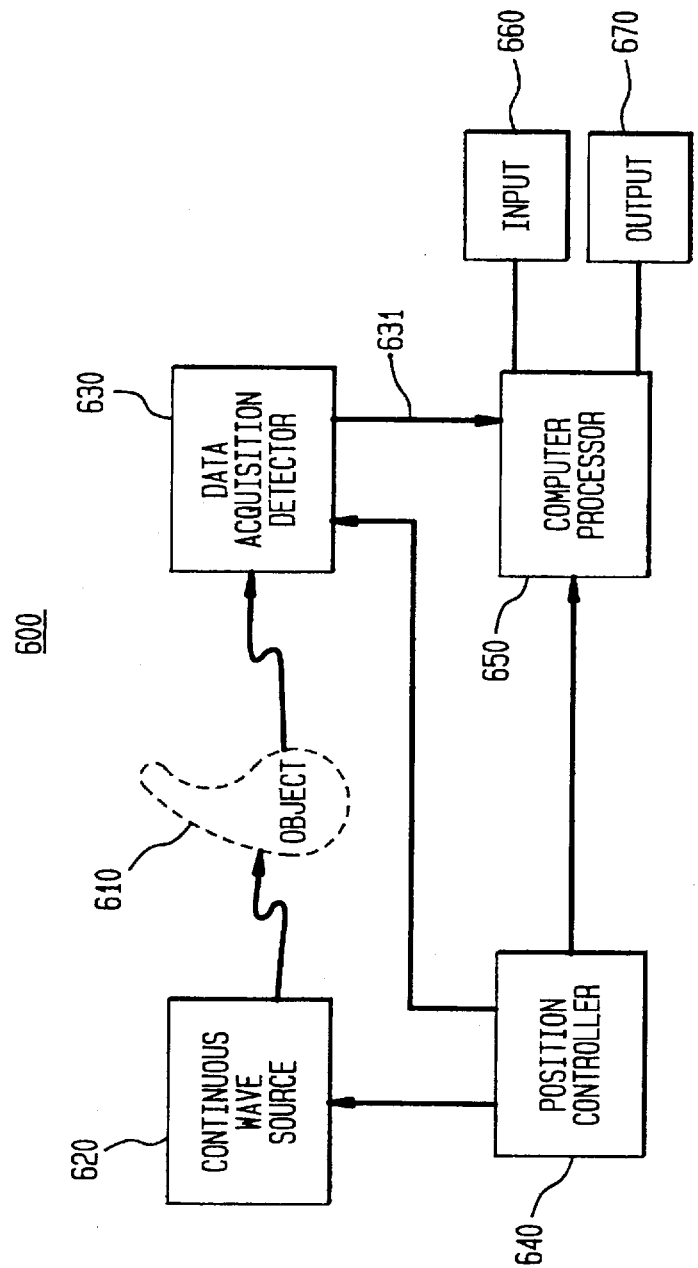
FIG. 6 illustrates a high-level block diagram of an illustrative embodiment of the tomography system in accordance with the present invention.

As depicted in high-level block diagram form in FIG. 6, system 600 is a direct reconstruction imaging system for generating an image of an object using measurements of transmitted radiation (e.g., photons) emanating from an object in response to photons impinging on the object. In particular, object 610 is shown as being under investigation. System 600 is composed of: CW source 620 for irradiating object 610; data acquisition detector 620 for generating the transmitted intensity of radiation emanating from object 610 at one or more strategic locations proximate to object 610, such transmitted intensity being determined from measurements of both the modulus and phase (to obtain $T_{ac}$) via a phase-sensitive detector; position controller 640 for controlling the location of detector 630 relative to source 620; and computer processor 650, having associated input device 660 (e.g. a keyboard) and output device 670 (e.g., a graphical display terminal). Computer processor 650 has as its inputs positional information from controller 640 and the measured transmitted intensity from detector 630.

Source 620 and data acquisition detector 630 of system 600 are realized with conventional components; illustratively, Gratton discloses such source and detector arrangements, and the teachings of Gratton with respect to the measurement procedure are hereby incorporated with reference. Thus, for example, CW source 620 is composed of a conventional near infrared laser operating in the 600 to 1200 nm region and at a power level of approximately 10 watts such as provided by a mode-locked Neodymium YAG laser (Antares, model 76S-ML-SHG). Detector 630 is, for instance, composed of a image intensifier (such as provided by Princeton Instruments, Inc., OMA detector model IRY512 G/RB) which feeds a CCD-type television camera (such as provided by ITT, Fort Wayne, Ind., model CCD F144). With the arrangements disclosed by Gratton, both the phase and modulus of the diffusively scattered radiation may be generated.

Position controller 640 is utilized whenever CW source 620 and/or data acquisition detector 630 may be composed of a plurality of radiation sources and detectors, respectively, in order to control which of the plurality of sources may be energized for a given time period and which of the plurality of detectors may be activated during a prescribed time interval. As will be discussed in more detail below, in a practical implementation of the direct reconstruction imaging technique, it is oftentimes necessary to measure the transmitted intensity effected by a number of source-detector positions surrounding object 610. For the sake of expediency, generation of the required transmitted intensity data is expeditiously accomplished by having arrays of P laser sources and Q photon detectors. Accordingly, source 620 may be composed, in its most general implementation, of P CW sources or the like arranged strategically around the periphery of object 610. Similarly, data acquisition detector may be composed, in its most general realization, of Q radiation detectors or the like also arranged strategically around the periphery of object 610 and in a cooperative relation with the P sources.

The point of departure between the inventive subject matter herein and the prior art resides in the processing of the measured data. Computer 650 stores a computer program which implements the direct reconstruction algorithm; in particular, the stored program processes the measured transmitted intensity data to produce the image of the object under study using a prescribed mathematical algorithm; the algorithm is determined with reference to the integral operator relating the transmitted intensity to both the absorption and the diffusion coefficients. The processing effected by computer 650 is the focus of the discussion of the methodology section of this description, which follows immediately.

B. METHODOLOGY

B.1 Computational Model

The fundamental integral equation expressed by equation (5), repeated here, $$-\ln T_{ac}(x_1,x_2) = \int d^3x \Gamma_A(x;x_1,x_2)\alpha(x) + \int d^3x \Gamma_D(x;x_1,x_2) D(x), \quad (5)$$

is specifically referred to herein as the Schotland's Third Frequency-Domain Integral Equation.

In general, equation (5) holds for each set of measurements made with pre-determined source and detector positions; for a first set of measurements, equation (5) has the following form:

$$\int K_{11}(x,x')f_1(x')d^3x' + \int K_{12}(x,x')f_2(x')d^3x' = g_1(x); \quad (12)$$

similarly, for a second set of measurements, the following obtains:

$$\int K_{21}(x,x')f_1(x')d^3x' + \int K_{22}(x,x')f_2(x')d^3x' = g_2(x); \quad (13)$$

Relations (12) and (13) may be summarized in the general form $$Kf = g \quad (14)$$

where K is a matrix of integral operators and f,g are vectors of elements in appropriately selected function spaces. Equation (14) is said to be ill-posed if (a) it is not solvable, (b) a unique solution does not exist, or (c) the solution does not depend continuously on the data. The latter case (c) is of primary interest in the numerical study of ill-posed problems because it may lead to numerical instability. This is particularly important if the data is imprecisely known or is the subject to statistical uncertainties, such as measurement inaccuracy or noise, which would be the situation for measurements for imaging. There are methods for conditioning ill-posed problems. First, if the solution does not exist, the minimizer of $\|Kf-g\|$ is defined as a solution. Non-uniqueness is handled by choosing the minimizer with the least norm. Finally, continuity is restored by introducing "regularization" to the solution procedure.

Solving for the minimizer with the least norm yields the "normal equation" relating to equation (14); the normal equation is of the form $$K^*Kf = K^*g, \quad (15)$$

where $K^*$ is the adjoint of K, and the property that $K^*K$ is self-adjoint has been employed. Thus, a solution for f in equation (14) is of the following form:

$$f = (K^*K)^{-1}K^*g \equiv K^+g. \quad (16)$$

From equation (16), $$K^+ = (K^*K)^{-1}K^* \quad (17)$$

is called the "generalized inverse" of K.

B.2 Singular Value Decomposition

If K is such that a mapping from $H_1$ to $H_2$ occurs, where $H_1$ and $H_2$ are Hilbert spaces, then $K^*K$ is a self-adjoint, positive operator. If the eigenfunctions and eigenvalues of $K^*K$ are denoted by $\{f_n\}$ and $\{\sigma_n^2\}$, respectively, then the following relation obtains: $K^*Kf_n = \sigma_n^2 f_n$.

The $\{\sigma_n\}$ are the singular values of K. Also, the $\{f_n\}$ form a basis for $H_1$. The singular values are ordered as $\sigma_1^2 \geq \sigma_2^2 \geq \ldots \geq 0$, where multiplicities are counted and 0 can appear with infinite multiplicity.

If $\{g_n\}$ is defined by $$Kf_n = \sigma_n g_n, \quad (18)$$

then the $\{g_n\}$ are a basis for Hilbert space $H_2$. Moreover, it then follows that $$K^*g_n = \sigma_n f_n. \quad (19)$$

To derive the singular value decomposition of K, put K in the form $$K = I_{H2} K I_{H1} \quad (20)$$

and use the identities $$I_{H1} = \sum_n f_n \hat{\otimes} f_n \quad (21)$$

and $$I_{H2} = \sum_n g_n \hat{\otimes} g_n \quad (22)$$

where $\hat{\otimes}$ denotes the tensor product. Manipulation of equations (20)–(22) leads to $$K = \sum_n \sigma_n g_n \hat{\otimes} f_n. \quad (23)$$

Equation (23) is called the "singular value decomposition" of K.

The singular value decomposition of equation (23) can now be used to obtain a form for the generalized inverse $K^+$ of equation (17). As a result of equation (23), $$K^*K = \sum_n \sigma_n^2 f_n \hat{\otimes} f_n \quad (24)$$

and $$K^* = \sum_n \sigma_n f_n \hat{\otimes} g_n, \quad (25)$$

then it directly follows, after substitution of equations (24) and (25) into equation (17), that $$K^+ = \sum_n \frac{1}{\sigma_n} f_n \hat{\otimes} g_n. \quad (25)$$

Now, using equations (16) and (26), the solution of Kf=g is $f = K^+ g$, which is of the form $$f = \sum_n \frac{1}{\sigma_n} <g_n, g> f_n. \quad (27)$$

If some of the $\sigma_n$'s vanish, then $K^+$ is not well-defined and, in particular, is not continuous. To resolve this anomaly, the regularization procedure is introduced.

B.3 Regularization

To condition the singular value decomposition, the following expression is now defined:

$$K_\beta^+ = \sum_n R_\beta(\sigma_n) f_n(x) g_n, \quad (28)$$

where the regularizer $R_\beta(\sigma)$ has the properties (i) $R_\beta(\sigma) \to 1/\sigma$ as $\beta \to 0^+$;

(ii) $R_\beta(\sigma) \sim 1/\sigma$ for $\sigma >> 0$ (with $\beta > 0$); \quad (29)

(iii) $R_\beta(\sigma) \to 0$ as $\sigma \to 0$ (with $\beta > 0$).

For instance, two natural choices (others are possible) include:

(a) $R_\beta(\sigma) = 1/\sigma$ for $\sigma > \beta$; otherwise, $R_\beta(\sigma) = 0$; \quad (30)

(b) $R_\beta(\sigma) = \sigma/(\beta + \sigma^2)$. \quad (31)

(One typical heuristic criterion is to set $\beta \sim O(\sigma_1)$.)
Thus the solution of equation (14) may be written as $$f(x) = \int d^3x' K_\beta^+(x, x') g(x') \quad (32)$$

where $$K_\beta^+(x, x') = \sum_n R_\beta(\sigma_n) f_n(x) g_n(x'). \quad (33)$$

B.4 Numerical Solution of the Schotland's Third Integral Equation

The above developments for the formal solution of a general Fredholm equation of the first kind, including the techniques of singular value decomposition and regularization, may now be applied to implement the numerical solution of equation (5)—Schotland's Third Integral Equation:

$$-\ln T_{\alpha c}(x_1, x_2) = \int d^3x \Gamma_A(x; x_1, x_2) \alpha(x) + \int d^3x \Gamma_D(x; x_1, x_2) D(x). \quad (5)$$

For a three-dimensional object, denoted $\Omega$, it is supposed that there are P sources and Q detectors used to probe the object. These sources are spaced about the periphery of the object and, operating in conjunction with the sources, there are suitably placed detectors. For the sake of simplicity, a single frequency is considered in the following exposition. In general, the results may be readily extended to the case of multiple frequencies. Let i, i=1,2, ..., P and j, j=1,2, ..., Q be indices corresponding to the P sources and Q detectors; then, for a given frequency, equation (5) becomes:

$$-\ln T_{ij} = \int d^3x (\Gamma_A)ij(x)\alpha(x) + \int d^3x(\Gamma_D)ij(x)D(x). \quad (34)$$

Now $\Gamma_A, \Gamma_D, \alpha$ and D are discretized by decomposing $\Omega$ into "voxels" (i.e., volume elements having basically equal sides) $C_m$, m=1,2, ..., M which cover the object. It is then assumed that the granularity is such that f and $\Gamma$ are constant in each box. To recast equation (34) in a standard form, the following identifications are made:

$$|C_m|(\Gamma_A)ij(x_m) \equiv A_{ij}^m, \quad (35)$$

$$|C_m|(\Gamma_D)ij(x_m) \equiv B_{ij}^m, \quad (36)$$

$$\alpha(x_m) \equiv a_m, \; D(x_m) \equiv b_m, \quad (37)$$

and $$-\ln T_{ij} \equiv c_{ij}, \quad (38)$$

where $|C_m|$ is the volume of a voxel, $a_m$ is the strength of $\alpha(x_m)$ at the middle of the $m^{th}$ voxel, and $b_m$ is the strength of $D(x_m)$ at the middle of the $m^{th}$ voxel. Then, using these definitions, equation (34) becomes $$\sum_m A_{ij}^m a_m + \sum_m B_{ij}^m b_m = c_{ij}. \quad (39)$$

for m=1,2, ..., M; i=1,2, ..., P; and j=1,2, ..., Q. For instance, to illustrate equation (39) in long form, without loss of generality, let P=Q=2 and M=3:

$$A_{11}^1 a_1 + A_{11}^2 a_2 + A_{11}^3 a_3 + B_{11}^1 b_1 + B_{11}^2 b_2 + B_{11}^3 b_3 = c_{11} \quad (40a)$$

$$A_{11}^2 a_1 + A_{12}^2 a_2 + A_{12}^3 a_3 + B_{12}^1 b_1 + B_{12}^2 b_2 + B_{12}^3 b_3 = c_{12} \quad (40b)$$

$$A_{13}^1 a_1 + A_{13}^2 a_2 + A_{13}^3 a_3 + B_{13}^1 b_1 + B_{13}^2 b_2 + B_{13}^3 b_3 = c_{13} \quad (40c)$$

$$A_{14}^1 a_1 + A_{14}^2 a_2 + A_{14}^3 a_3 + B_{14}^1 b_1 + B_{14}^2 b_2 + B_{14}^3 b_3 = c_{14} \quad (40d)$$

(The above set of four equations, referred to as equation (40), is presented merely for illustrative purposes since it should be noted that set (40) has four equations and six unknowns, that is, the set is "underdetermined". However, it is possible to generate additional equations so as to "overdetermine" the system, as now discussed.) The above set of four equations may be written as Sx=c, where x is a column vector expressed as follows:

$$x = \begin{pmatrix} a_1 \\ a_2 \\ a_3 \\ b_1 \\ b_2 \\ b_3 \end{pmatrix}$$

and S is a matrix of coefficients appropriate to equation (40). Accordingly, the matrix form of equation (39) is represented as Sx=c, where S is a (PQ by 2M) matrix, that is, equation (39) yields PQ equations in 2M unknowns. It is preferable to "overdetermine" equation (39) by having PQ>2M, or by using multiple time points for each source-detector pair. If there are K time points, then matrix S is (KPQ by 2M) matrix. Typically in practice KPQ=6M.

The solution of singular value decomposition applied to a matrix formulation is a well-known technique. For example, a procedure for singular value decomposition is described in the text "Numerical Recipes", by Press, Flannery, Teukolsky, and Vettering, 1986, Cambridge University Press, Cambridge, England. A commercially available software package implementing the singular value decomposition, called Interactive Data Language (IDL) available from Research Systems Inc. of Denver, Colo., may be used in practice; IDL was specifically designed for scientific computations, especially image processing applications. With IDL, a subroutine-like call of the form "SVD [Matrix]" (e.g. SVD [S]) in terms of the above S matrix returns the singular values which may then be used to solve the system of linear equations.

Once the singular value decomposition has been effected, regularization according to equation (33) is readily accomplished in order to obtain the regularized, generalized inverse for the matrix S, which is denoted $S^+$. The solution to the discretized Schotland's Third Integral Equation becomes $x=S^+c$.

C. FLOW DIAGRAMS

Figure 7:
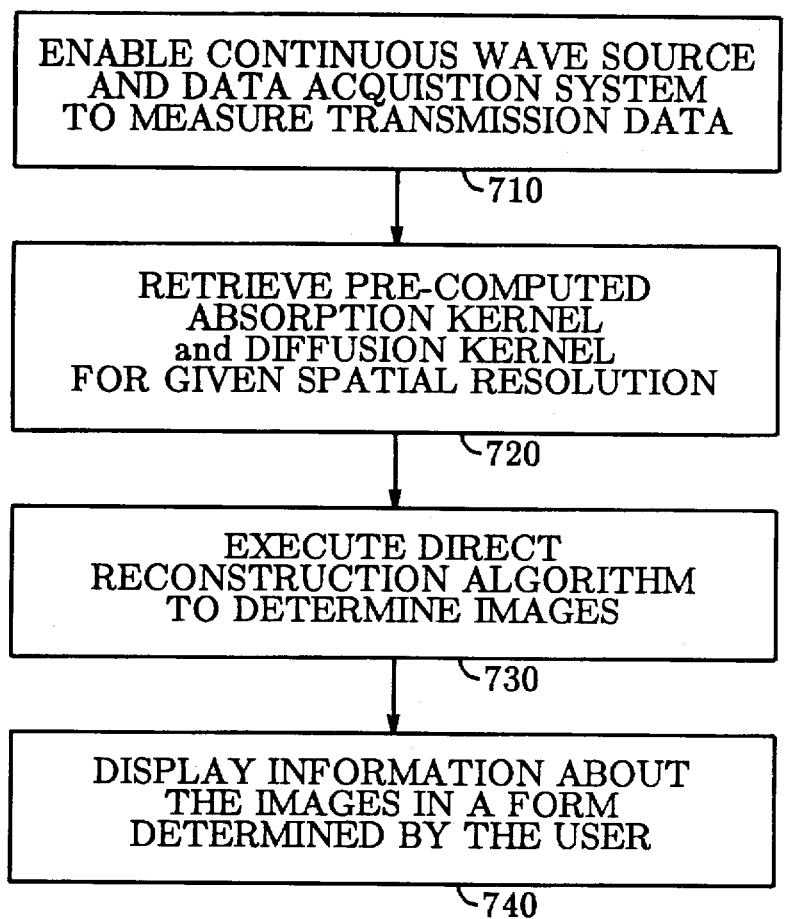
FIG. 7 is a high-level flow diagram of the methodology of the present invention.
Figure 9A:
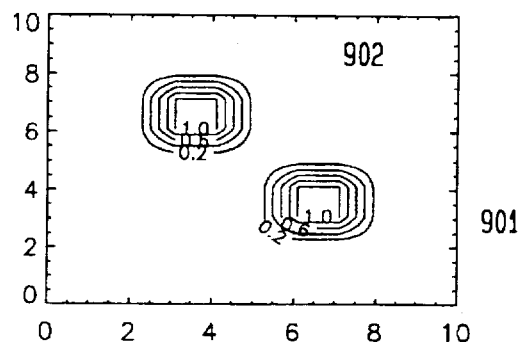
FIG. 9 shows a reconstructed exemplary object for imaging both absorption and diffusion.
Figure 9B:
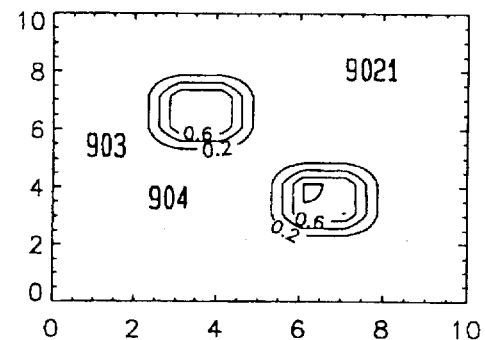
Figure 9C:
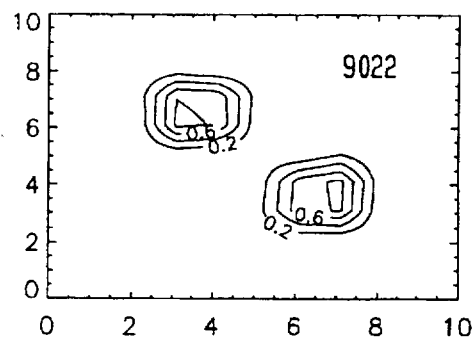
Figure 9D:
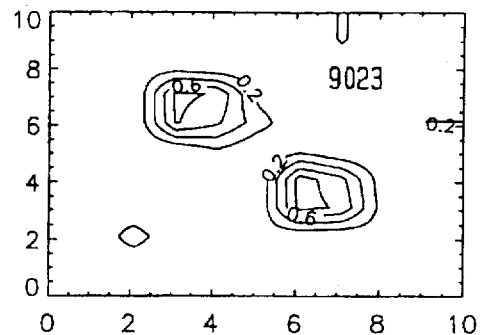
Figure 9E:
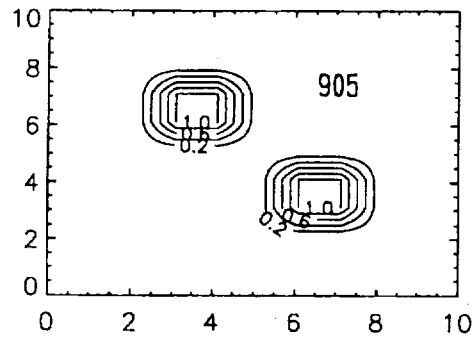
Figure 9F:
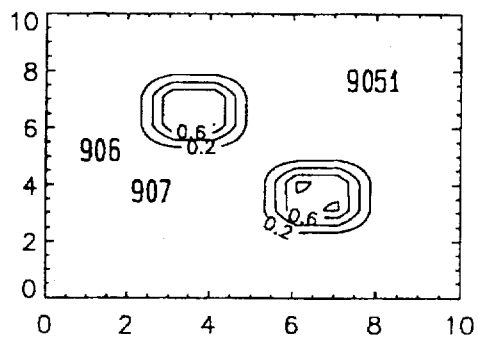
Figure 9G:
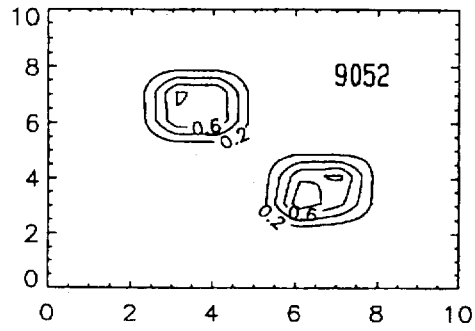
Figure 9H:
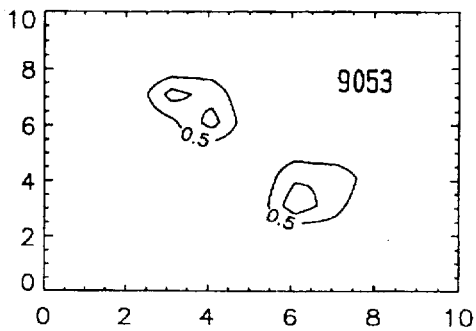

The methodology discussed in the previous section is set forth in high-level flow diagram 700 in FIG. 7 in terms of the illustrative embodiment of the system shown in FIG. 6. With reference to FIG. 7, the processing effected by control block 710 enables photon source 620 and data acquisition system 630 so as to measure energy emanating from object 610 due to CW source 620. These measurements are passed to computer processor 650 from acquisition system 630 via bus 631. Next, processing block 720 is invoked to retrieve the pre-computed and stored absorption and diffusion kernels as expressed by equations (6) and (9), respectively. In turn, processing block 730 is operated to execute the direct reconstruction algorithm set forth with respect to equations (12)–(39), thereby determining the absorption coefficient $\alpha(x)$ and the diffusion coefficient $D(x)$. Finally, as depicted by processing block 740, the reconstructed images corresponding to the absorption coefficient $\alpha(x)$ and the diffusion coefficient $D(x)$ is provided to output device 670 in a form determined by the user; device 670 may be, for example, a display monitor or a more sophisticated three-dimensional video display device.

One illustrative manner of carrying out the direct reconstruction exhibited by block 720 is further depicted by high-level flow diagram 800 of FIG. 8. In particular, processing block 810 shows that the first step is to form the kernel matrix S, namely, from the A coefficients as determined by discretization, that is, $A_{ij}^m$ for $m=1,2,\ldots,M$; $i=1,2,\ldots,P$; $j=1,2,\ldots,Q$, as well as the B coefficients as determined by discretization, that is, $B_{ij}^m$ for $m=1,2,\ldots,M$; $i=1,2,\ldots,P$; $j=1,2,\ldots,Q$. Next, processing block 820 is invoked to compute the singular value decomposition of the kernel matrix S. Then, processing block 830 is executed to generate the regularized, generalized inverse. Finally, block 840 is invoked to obtain the solution $x=S^+c$.

With reference to FIG. 9, there is shown the reconstruction of an exemplary object. In particular, FIG. 9(a) shows an original two-dimensional object 902 embedded in a 10 cm×10 cm specimen 901. FIGS. 9(b)–(c) show the direct reconstruction of the absorption image 902 (e.g., 9021–9023 in FIGS. 9(b)–(c), respectively) in the presence of additive Gaussian noise of 0.1%, 1% and 5% to indicate the relative insensitivity of the direct reconstruction to noise. Also, in particular, FIG. 9(e) shows an original two-dimensional object 905 embedded in a 10 cm×10 cm specimen 901. FIGS. 9(f)–(h) show the direct reconstruction of the diffusion image 905 (e.g., 9051–9053 in FIGS. 9(f)–(h), respectively) in the presence of additive Gaussian noise of 0.1%, 1% and 5% to indicate the relative insensitivity of the direct reconstruction to noise. In this example, $\alpha_0=1.0$ cm$^{-1}$ and $D_0=1.0$ cm$^2$ ns$^{-1}$ and the contour levels 903 and 904 as well as 905 and 907 refer to the fluctuation in the absorption coefficient measured in units of cm$^{-1}$ and diffusion coefficient in units of cm$^2$ns$^{-1}$, respectively. The transmission coefficients were obtained using Monte Carlo simulations.

The system and methodology described utilizes the free-space model of the absorption and diffusion kernels so that the kernels are pre-computed and stored in computer processor 650 for recall during the reconstruction process. This is appropriate when object 610 is surrounded by an arrangement, such as a thin, rubber-like container filled with a substance (e.g., the commercially available medical product called Intralipid), so that the arrangement provides a spatial extent external to the object that effectively gives rise to a free-space condition surrounding the object. The object's actual boundary (e.g., a human skull during imaging of brain) becomes merely another shape that is determined by the direct reconstruction procedure. Intralipid is useful because it is a colloidal substance wherein particles in the range of 0.5 microns to 2 microns are suspended, and the substance, as packaged, does not rapidly deteriorate; moreover, the $l^*$ of such a substance is readily measurable.

Whereas the above formulation has focused on the case of amplitude modulation, that is, $\omega \neq 0$, the formulation also applies for so-called DC imaging, that is, the case wherein $\omega=0$. Thus both cases, namely, AC imaging ($\omega \neq 0$) and DC imaging ($\omega=0$) are encompassed by the terminology "continuous wave."

Also, whereas the above formulation has focused on the case of reconstruction from measurements of $T_{ac}$, it is possible to formulate the direct reconstruction methodology in terms of the transmission coefficient $T_{mod}$ where $$T_{mod}=|u_\omega(x)|/|u_\omega^0(x)|. \qquad (41)$$

With this formulation, only measurements of the modulus are required, thereby precluding reconstruction perturbations that may occur because of phase measurement inaccuracies in generating $T_{ac}$. The integral equation using the modulus alone may be obtained as follows:

$$-\ln T_{mod}(x_1,x_2)=\int d^3 x \Gamma_{Amod}(x;x_1,x_2)\alpha(x)+\int d^3 x \Gamma_{Dmod}(x;x_1,x_2)D(x), \qquad (42)$$

where $$\Gamma_{Amod}(x;x_1,x_2) = \frac{1}{2}(\Gamma_A(x;x_1,x_2)+\Gamma_A^*(x;x_1,x_2)), \qquad (43)$$

and $$\Gamma_{Dmod}(x;x_1,x_2) = \frac{1}{2}(\Gamma_D(x;x_1,x_2)+\Gamma_D^*(x;x_1,x_2)). \qquad (44)$$

Similarly, reconstruction based only on phase measurements may be performed; in this situation, the following integral equation obtains:

$$\phi(x_1,x_2)-\phi_0(x_1,x_2)=\int d^3 x \Gamma_{A\phi}(x;x_1,x_2)\alpha(x)+\int d^3 x \Gamma_{D\phi}(x;x_1,x_2)D(x), \qquad (45)$$

where $$\Gamma_{A\phi}(x;x_1,x_2) = \frac{1}{2i}(\Gamma_A(x;x_1,x_2)-\Gamma_A^*(x;x_1,x_2)), \qquad (46)$$

where $$\Gamma_{D\phi}(x;x_1,x_2) = \frac{1}{2i}(\Gamma_D(x;x_1,x_2)-\Gamma_D^*(x;x_1,x_2)). \qquad (47)$$

and where $\phi_0(x_1,x_2)$ is the reference phase measured in the absence of absorption.

Whereas the above discussion has focused on obtaining modulus and phase information utilizing frequency domain measurements, it will be readily appreciated by one of ordinary skill in the art that a time domain source may be utilized to obtain, for example, a transmitted intensity due to a pulsed source, and that such measured intensity may then be converted to the frequency domain by a transformation process such as a Fourier Transform.

It is to be understood that the above-described embodiment is simply illustrative of the application of the principles in accordance with the present invention. Other embodiments may be readily devised by those skilled in the art which may embody the principles in spirit and scope. Thus, it is to be further understood that the methodology described herein is not limited to the specific forms shown by way of illustration, but may assume other embodiments limited only by the scope of the appended claims.

What is claimed is:

1. A method for generating absorption and diffusion images of an object comprising the steps of irradiating the object with a continuous wave source of radiation, measuring a transmitted intensity due predominantly to diffusively scattered radiation wherein said transmitted intensity is related to an absorption coefficient and a diffusion coefficient by an integral operator, and directly reconstructing the images by executing a prescribed mathematical algorithm, determined with reference to said integral operator, on said transmitted intensity, said step of directly reconstructing including the step of computing an absorption kernel and a diffusion kernel.

2. The method as recited in claim 1 wherein the step of irradiating the object includes the step of successively irradiating the object with different wavelengths.

3. A system for generating absorption and diffusion images of an object comprising continuous wave radiation source means for irradiating the object, detector means for measuring a transmitted intensity due predominantly to diffusively scattered radiation wherein said transmitted intensity is related to an absorption coefficient and a diffusion coefficient by an integral operator, and means for directly reconstructing the images by executing a prescribed mathematical algorithm, determined with reference to said integral operator, on said transmitted intensity, said means for directly reconstructing including means for computing an absorption kernel and a diffusion kernel.

4. The system as recited in claim 3 wherein said source means for irradiating the object includes means for successively irradiating the object with different wavelengths.

* * * * *